United States Patent [19]

Schneider et al.

[11] 4,086,284
[45] Apr. 25, 1978

[54] ISOMERIZATION OF ENDO-TETRAHYDRODICYCLOPENTADIENE TO A MISSILE FUEL DILUENT

[75] Inventors: Abraham Schneider, Overbrook Hills; Richard E. Ware, Aston; Edward J. Janoski, Havertown, all of Pa.

[73] Assignee: Suntech, Inc., Wayne, Pa.

[21] Appl. No.: 720,307

[22] Filed: Sep. 3, 1976

[51] Int. Cl.² .................................................. C07C 1/00
[52] U.S. Cl. ................................. 260/666 PY; 60/208
[58] Field of Search .................... 260/666 PY; 60/208, 60/211; 149/109.4, 109.6

[56] References Cited

U.S. PATENT DOCUMENTS 3,864,178  2/1975  Rudy et al. .................. 149/109.6 X Primary Examiner—Stephen J. Lechert, Jr.
Attorney, Agent, or Firm—J. Edward Hess; Donald R. Johnson; Anthony Potts, Jr.

[57] ABSTRACT

Endo-tetrahydrodicyclopentadiene is isomerized to its exo-isomer in the presence of aluminum trichloride at a temperature in the range between from about 20° C to about 90° C. The mole ratio of $AlCl_3$ to the tetrahydrodiene is in the range between from about 0.001 to about 0.75. An inert solvent may also be used. The very facile isomerization is essentially quantitative. The exo-isomer has utility as a relatively high BTU/gallon, viscosity-lowering difluent for a missile fuel.

10 Claims, No Drawings

ISOMERIZATION OF ENDO-TETRAHYDRODICYCLOPENTADIENE TO A MISSILE FUEL DILUENT

BACKGROUND OF THE INVENTION

The invention herein described was made in the course of or under a contract hereunder with the United States Air Force Systems Command.

CROSS REFERENCES TO RELATED APPLICATIONS

This application is related to the following applications filed same date:

| Ser. No. | Inventors | Title |
| --- | --- | --- |
| 720,306 | Edward J. Janoski, et al | Isomerization of Tetrahydropolycyclopentadiene to a Missile Fuel Additive |
| 720,308 | Richard E. Ware, et al | Isomerization of Tetrahydroticyclopentadiene to a Missile Fuel. |
| 720,305 | Abraham Schneider, et al | Process for Improving Low Temperature Properties of Tetrahydroalkyldicyclopentadienes |

This invention relates to preparation of exo-tetrahydrodicyclopentadiene, hereinafter referred to as exo-THDCPD. More particularly the invention relates to the isomerization of endo-tetrahydrodicyclopentadiene, i.e. endo-THDCPD, a solid, to its liquid isomer, exo-THDCPD. Still more particularly the invention relates to the isomerization of endo-THDCPD to exo-THDCPD using a certain amount of aluminum chloride and operating at a temperature range which causes a rapid and an almost complete isomerization.

The resulting isomeric liquid mixture can be used as a diluent for high density missile fuel. This it can be blended with such a fuel to lower its viscosity and freezing point or pour point without excessively reducing its BTU content. Such fuels can be used in either jet or rocket propulsion. Jet propulsion includes a jet engine which can be used for missile, aircraft and others and includes the three basic types, i.e., ramjet, turbo-jet and pulse jet. The term rocket generally refers to a device containing its own oxygen or oxidizing agent. An article in Aviation Week and Space Technology, Jan. 26, 1976, pages 111–113, discloses some of the high density hydrocarbon fuels that have been modified by the diluent disclosed herein.

U.S. Pat. No. 3,381,046 discloses the isomerization of endo-tetrahydrodicyclopentadiene to its exo-isomer using sulfuric acid. It also suggests that a Lewis acid such as aluminum chloride may be used, however, it cautions that the isomerization can proceed beyond the exo form to form decalin and adamantane.

SUMMARY OF THE INVENTION

Unexpectedly it has been discovered that endo-THDCPD can be easily isomerized to its exo-isomer in the presence of a small amount of anhydrous aluminum trichloride at a low temperature such that no measurable decalin and/or adamantane is formed. Further, the isomerization is essentially quantitative and reaction time is relatively short. Use of an inert solvent is optional.

DESCRIPTION

The feed to the isomerization process is endo-THDCPD. Its configuration is as follows:

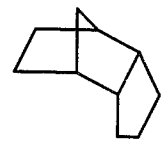

The product resulting from the isomerization is exo-THDCPD which has the following configuration:

Surprisingly the above reaction can be controlled so that the production of undesirable products such as decalin and/or adamantane can be avoided. Further surprising is that the reaction can take place in a relatively short time. Still further surprising is that the reaction is essentially quantitative.

The endo-THDCPD feed can contain other similar hydrocarbons. However, such similar hydrocarbons should not adversely effect the isomerization or the catalyst. In addition the similar hydrocarbon should not adversely influence the resulting properties of the exo-THDCPD. Thus for optimum results the feed consists essentially of endo-THDCPD.

The catalyst for isomerization is anhydrous $AlCl_3$. Any material which could adversely affect its effectiveness during the isomerization should not be present. For example, the presence of hydroxylic compounds such as water, alcohol or oxygen from air could deactivate the $AlCl_3$.

The amount of $AlCl_3$ used is that which is sufficient to control the isomerization. This control results in that no measurable amount of decalin and/or adamantane is formed. Thus the mole ratio of $AlCl_3$ to endo-THDCPD can vary and while a mole ratio range between from about 0.001 to about 0.75 is operative, a preferable range is between from about 0.01 to about 0.2.

An inert solvent can be used in the isomerization. The solvent dissolves the endo-THDCPD. Since the reaction is mildly exothermic the solvent can serve as a heat sink. The solvent can also facilitate the handling of the solid endo-THDCPD. The solvent can also facilitate the isomerization until sufficient exo-THDCPD is formed to dissolve its endo-precursor. The inert solvent should not adversely react with the feed, product or $AlCl_3$. Suitable inert solvents include chlorinated paraffins such as methylene dichloride, tetrachloroethane, pentachloroethane and paraffins such as hexane, pentane and the like. As to the amount of solvent used, excessive amounts can decrease the reaction rate and thus adversely effect the economics of a commercial operation. In addition to an inert solvent exo-THDCPD can serve in the same capacity. However, typically the weight ratio of the amount of solvent to the amount of THDCPD is in the range between from about 0.25 to about 1.5.

The isomerization temperature needs to be controlled between a narrow range. The lower limit can be influenced by the freezing point of the solvent and/or the rate of the reaction. However, while the reaction can proceed at a very low temperature the rate could be so slow as to be commercially unattractive. Thus, generally the lower temperature limit is about −20° C with about 10° C preferred. The upper limit is controlled by the formation of undesirable products which adversely effect the properties of the resulting missile fuel. Also if the reaction rate is too rapid at an elevated temperature an uncontrolled exotherm could result. Thus, generally the upper temperature limit is about +90° C with about +70° C preferred.

Sufficient reaction time depends in part on the amount of the tetrhydrodiene isomerized, the amount of stirring, the amount of $AlCl_3$ used, the configuration of the vessel containing the reaction or contacting mixture, and other variables. Since the amount of isomerization can be monitored during the isomerization, for example, by measuring the viscosity, when the desired amount of isomerization is obtained the reaction can be stopped. Generally substantially all of the endo-THDCPD is isomerized to exo-THDCPD. However it would be preferred to isomerize at least about 90% of the endo-THDCPD while at least about 70% would be operative. The latter is particularly so if the engine used heated tanks for holding the fuel.

After the reaction has been stopped the solvent can be removed. If the solvent has a relatively low boiling point it can be easily boiled off. After the solvent is removed the $AlCl_3$ and hydrocarbon tar, if any, can be easily separated, for example, by decantation. The tar and $AlCl_3$ together are often referred to as sludge. Also, any unreacted feed may be separated by distillation from the washed product. However, some endo-THDCPD can remain since the exo-isomer is a suitable solvent for it. Then a washing of the exo-THDCPD would remove any remaining $AlCl_3$. Other means can be used to recover the isomeric tetrahydrodiene from the solvent and sludge. However leading the sludge in place in a reactor after removing the hydrocarbon phase, the sludge, fortified if necessary with an additional small quantity of fresh $AlCl_3$, can be used for isomerization of subsequent amount of endo-THDCPD.

The following examples illustrate embodiment of the present invention.

EXAMPLES

Three grams of essentially endo-THDCPD were placed in a 25 millileter Erlenmeyer flask along with 3.0 grams of methylene dichloride, a solvent. The tetrahydrodiene dissolved in the solvent. Then 1.8 grams of anhydrous $AlCl_3$ were added to the solution at room temperature and then the temperature of the solution was lowered to 0° C. The contents of the flask were stirred for 30 minutes at which time a sample was taken and treated to remove sludge. The treated sample was analyzed by vapor phase chromatography (vpc). After an additional 45 minutes another sample was taken, treated, and analysed and found to contain about 96% exo-THDCPD.

In another example 14 grams of essentially endo-THDCPD were placed in a 25 milliliter Erlenmeyer flask along with 10.2 grams of methylene dichloride. The resulting solution was chilled to 0° C. To the chilled solution 2.5 grams of anhydrous $AlCl_3$ were added. However, some HCl was released. It is believed that water or some other undesirable material was present which deactivated the $AlCl_3$. After 30 minutes another 6 grams of anhydrous $AlCl_3$ was added and at the end of the 30 minutes a sample, taken from the flask, was analyzed. This sample, after suitable treatment, was found to contain about 96% exo-THDCPD.

The following Table lists the properties of the two tetrahydrodienes.

TABLE

| THDCPD | Formula | Pour Point | Melting Point | Density | Heat of Combustion Net vol. BTU/gal |
|---|---|---|---|---|---|
| endo-THDCPD | $C_{10}H_{16}$ | — | 171° F (77° C) | 0.9563* | 144,794* |
| exo-THDCPD | $C_{10}H_{16}$ | −110° F | — | 0.9360 | 141,720 |

*Calculated

As can be seen from the Table the endo-THDCPD is a solid at ambient temperature whereas its exo-isomer is a liquid having a pour point of −110° F. Also, while there is a decrease in the heat of combustion, the decrease is relatively small.

Because of the aforementioned properties the exo-THDCPD can be used to correct deficiencies in existing missile fuels. Some of the fuels have, e.g. too high a pour point, for use at higher and colder altitudes. By diluting the aforementioned missile fuel with some of the exo-THDCPD mixture the resulting fuel will have an improved pour point without suffering from a substantial decrease in density.

Solvents, other then the aforementioned methylene dichloride, can be used with analogous results. Concentrations of $AlCl_3$ other then those used, will yield similar results.

The invention claimed is:

1. Process for isomerizing endo-tetrahydrodicyclopentadiene comprising:
    (a) contacting endo-tetrahydrodicyclopentadiene with anhydrous aluminum trichloride wherein the mole ratio of aluminum trichloride to the tetrahydrodiene is in the range between from about 0.001 to about 0.75 and the temperature of the contacting is in the range between from about −20° C to about 90° C;
    (b) continuing said contacting until at least 70% of the endo-tetrahydrodicyclopentadiene is isomerized to exo-tetrahydrodicyclopentadiene; and
    (c) recovering resulting product.

2. Process according to claim 1 wherein at least about 90% of the endo-tetrahydrodiene is isomerized to the exo-tetrahydrodiene.

3. Process according to claim 1 wherein the contacting takes place in the presence of exo-tetrahydrodicylcopentadiene.

4. Process according to claim 1 wherein the contacting takes place in the presence of an inert solvent or exo-tetrahydrodicyclopentadiene.

5. Process according to claim 4 wherein the inert solvent is selected from the group consisting of chlorinated paraffins and paraffins.

6. Process according to claim 4 wherein the mole ratio of aluminum trichloride to the endo-tetrahydrodiene is in the range between from about 0.01 to about 0.2.

7. Process according to claim 6 wherein the inert solvent is selected from the group consisting of hexane, pentane, methylene dichloride, tetrachloroethane, and pentachloroethane.

8. Process according to claim 7 wherein the exo-tetrahydrodicyclopentadiene is separated from contacting materials.

9. Process according to claim 7 wherein the temperature ranges between from about 10° C to about 70° C and substantially all of the endo-tetrahydrodiene is isomerized to the exo-tetrahydrodiene.

10. Process according to claim 1 wherein sludge, from a previous isomerization of the endo-tetrahydrodiene, fortified with a small quantity of fresh aluminum trichloride is used to contact and isomerize a subsequent amount of endo-tetrahydrodiene.

* * * * *